US006755811B1

(12) United States Patent
Constantz

(10) Patent No.: US 6,755,811 B1
(45) Date of Patent: Jun. 29, 2004

(54) METHODS AND DEVICES FOR REDUCING THE MINERAL CONTENT OF A REGION OF NON-INTIMAL VASCULAR TISSUE

(75) Inventor: Brent R. Constantz, Palo Alto, CA (US)

(73) Assignee: Corazon Technologies, Inc., Menlo Park, CA (US)

( * ) Notice: Subject to any disclaimer, the term of this patent is extended or adjusted under 35 U.S.C. 154(b) by 0 days.

(21) Appl. No.: 09/382,571

(22) Filed: Aug. 25, 1999

(51) Int. Cl.[7] .............................................. A61M 31/00
(52) U.S. Cl. ........................................ 604/500; 604/48
(58) Field of Search ......................... 604/48, 500, 506, 604/507, 508, 509, 511, 513

(56) References Cited

U.S. PATENT DOCUMENTS

| | | | |
|---|---|---|---|
| 4,636,195 A | * | 1/1987 | Wolinsky ..................... 604/53 |
| 5,744,153 A | | 4/1998 | Yewey et al. |
| 5,800,408 A | | 9/1998 | Strauss et al. |
| 5,927,284 A | | 7/1999 | Borst et al. |
| 5,968,726 A | | 10/1999 | Segall et al. |
| 6,044,845 A | | 4/2000 | Lewis |
| 6,290,689 B1 | * | 9/2001 | Delaney et al. ............. 604/507 |

OTHER PUBLICATIONS

Quiñones–Baldrich, et al. (Aug. 1993), "Very Distal Bypass for Salvage of the Severely Ischemic Extremity," *American Journal of Surgery* Vol. 166:117–123.
Semel, et al. (Jan. 1988), "Atraumatic Control in Calcified Arteries," *Annals of Vascular Surgery* vol. 2(1):73–74.
White, et al. (Aug. 1990), "Preparation of the Calcified Tibial Artery for Bypass Grafting," *Surgery–Gynecology and Obstetrics* vol. 171(2):165–166.

* cited by examiner

*Primary Examiner*—Manuel Mendez
(74) *Attorney, Agent, or Firm*—Bret E. Field; Bozicevic, Field & Francis

(57) ABSTRACT

Methods and devices for reducing the mineral content of a region of non-intimal vascular tissue are provided. In the subject methods, an isolated local environment that includes the region to be demineralized is produced. The pH of the local environment is then reduced to a subphysiologic level, e.g. by flushing with an acidic dissolution fluid, for a period of time sufficient for the mineral content of the region to be reduced. The devices of the subject invention are characterized by comprising a means for producing an isolated local environment that includes a non-intimal region of vascular tissue. Also provided are kits for practicing the subject methods.

15 Claims, 7 Drawing Sheets

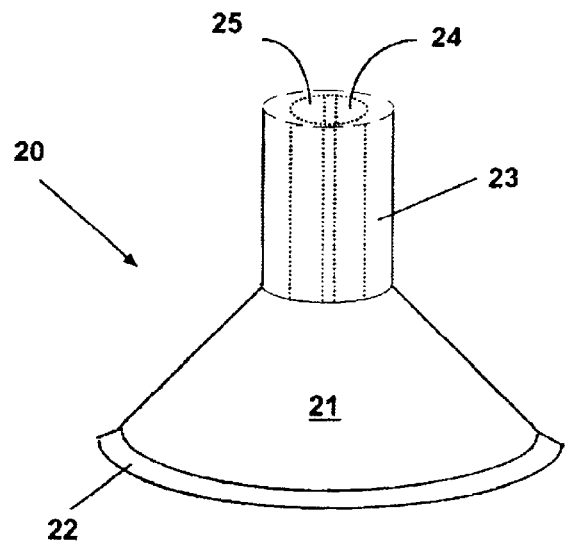
FIG. 2A
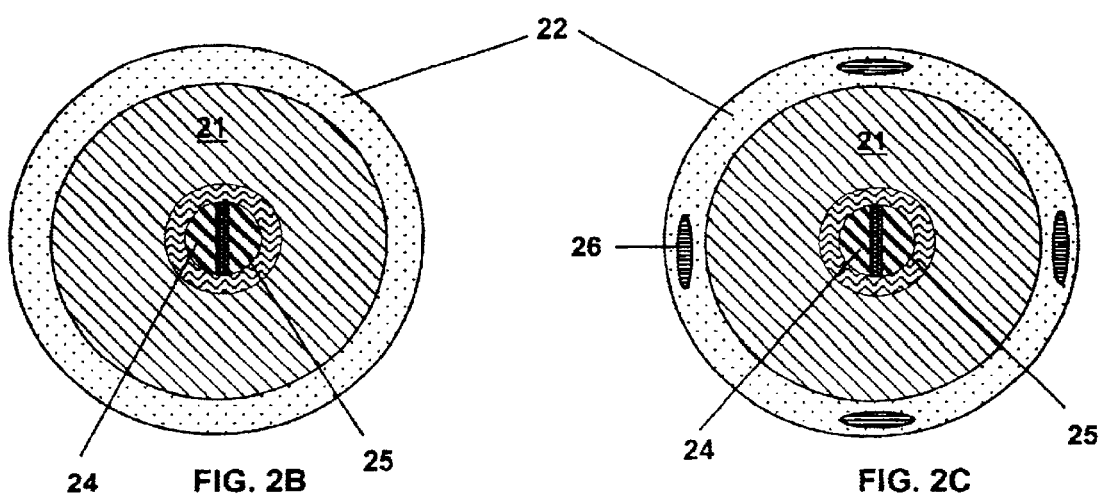
FIG. 2B
FIG. 2C

METHODS AND DEVICES FOR REDUCING THE MINERAL CONTENT OF A REGION OF NON-INTIMAL VASCULAR TISSUE

INTRODUCTION

1. Technical Field

The field of this invention is vascular anastomosis.

2. Background of the Invention

Anastomosis is a term used in medicine to describe the union or connection of one tubular structure to another so that the interiors of the tubular structures communicate with one another and transport fluid, e.g. blood, etc. There are generally two types of anastomoses: end-to-end and end-to-side. In an end-to-end anastomosis, the ends of two different tubular structures are joined together. In an end-to-side anastomosis, however, the severed end of one tubular structure is connected around an opening cut into the side of a second tubular structure. Anastomoses have been performed with a variety of different types of tubular structures or vessels in order to achieve a desired patient outcome. Typically, anastomoses are performed between airways, blood vessels, bowel segments, and urogenital tubes. The procedure for connecting blood vessels is referred to as vascular anastomosis.

One of the best known surgical procedures utilizing vascular anastomoses is the coronary artery bypass. In the context of coronary artery disease, the flow of oxygenated blood to the myocardium of the heart is impeded or compromised by a stenosis or obstruction in the coronary artery. This flow can be improved by providing a coronary artery bypass graft ("CABG") which diverts blood flow around the stenosis, thereby restoring myocardial circulation. In these procedures, a graft (e.g. a saphenous vein graft or a synthetic graft) is harvested and attached to the host vessel on either side of the stenosis utilizing an end-to-side anastomosis at each attachment site. Vascular anastomosis also finds use in the treatment of peripheral vascular occlusions, in which an occluded region of a peripheral vessel, usually an artery, is bypassed.

One problem experienced in anastomosis procedures is calcification of the anastomosis site, i.e. the presence of calcium phosphate mineral at the site of anastomosis. The presence of calcium phosphate mineral at an anastomotic site can render the vascular tissue at the site rigid and difficult to manipulate, and thereby potentially leading to complications during the anastomosis procedure.

Accordingly, there is interest in the development of a method to reduce the mineralization of vascular tissue at an anastomotic site. Of particular interest would be the development of such a method that was simple to perform and would make the anastomotic site more amenable to manipulation, e.g. would return the anastomotic state to a less rigid condition.

Relevant Literature

Articles discussing anastomosis at calcified vascular sites include: Quiñones-Badrich et al., Am. J. Surg. (August 1993) 166:117; Semel et al., Ann. Vasc. Surg. (January 1988) 2:73–74; and White & Gass, Surg. Gynecol. Obstet. (August 1990) 171:165–166.

SUMMARY OF THE INVENTION

Methods and devices are provided for at least reducing the mineral content of a region of non-intimal vascular tissue. In the subject methods, an isolated local environment is produced that includes the region of vascular tissue to be treated. The pH of the local environment is then maintained at a subphysiologic level for a period of time sufficient for the desired amount of demineralization to be accomplished. Also provided are devices capable of producing an isolated local environment that includes the target non-intimal region of vascular tissue. The subject methods and devices find use in a variety of applications, including the preparation of vascular anastomotic sites during vascular anastomosis procedures.

BRIEF DESCRIPTION OF THE DRAWINGS

FIGS. 2A to 2C provide a depiction of a first embodiment of a suction device for practicing the subject methods.

DESCRIPTION OF THE SPECIFIC EMBODIMENTS

Methods and devices are provided for reducing the mineral content of a region of non-intimal vascular tissue. In the subject methods, a region of non-intimal vascular in which demineralization is desired is isolated such that an isolated local environment that includes the target region of vascular tissue is produced. The pH of the local environment is then maintained at a subphysiologic level for a period of time sufficient for the desired amount of demineralization to occur. The devices of the subject invention are characterized by being capable of producing a substantially isolated local environment in situ that includes a region of vascular tissue, i.e. where the vascular tissue is still connected to the host. Also provided by the subject invention are systems and kits for practicing the subject methods.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

METHODS

The invention provides a method for at least reducing the mineral content of region of non-intimal vascular tissue by contacting the target region with a fluid capable of locally increasing the proton concentration in the local environment of the region. As used herein, the term "vascular" is used broadly to refer to the circulatory system of an organism. As such, the term "vascular" refers to arteries and veins, as well as specialized organs that are closely associated with the circulatory system, such as the heart. The term "cardiovascular" refers to that portion of the vascular system that is closely associated with the heart. Thus, target regions of the subject methods are regions of the vascular system, i.e. vascular tissue.

Figure 1:
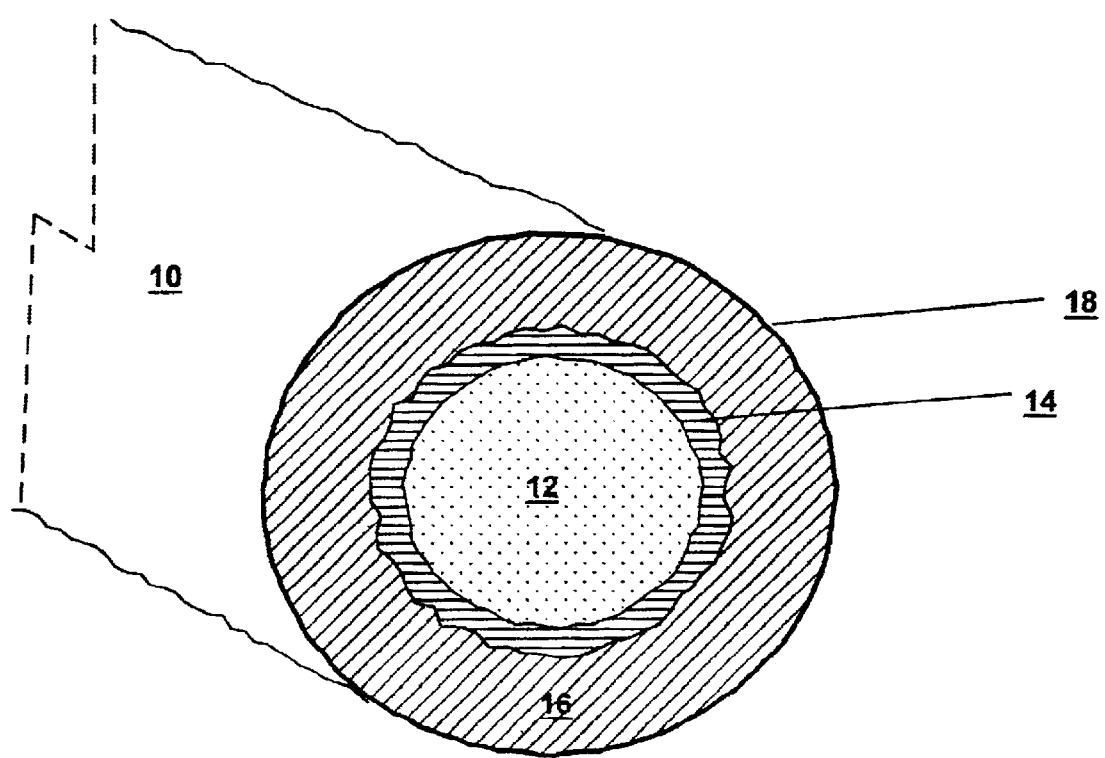
FIG. 1 provides a cutaway, cross-sectional view of an artery.

As specified above, the target region of the subject invention is a region of non-intimal vascular tissue, by which is meant that the region of vascular tissue is not a region of the intima, i.e. it is does not border the lumen of a blood vessel. As such, the target region of the subject methods does not come into direct contact with blood. Target vascular tissue of the subject methods therefore includes the media of a blood vessel, the adventitia of a blood vessel, etc. See FIG. 1. (In FIG. 1, vessel 10 includes lumen 12 bordered by intima 14, which in turn is bordered by media 16 and finally adventitia 18).

The target region of non-intimal vascular tissue that is the subject of the present methods is a region of vascular tissue characterized by the presence of one or more different types of minerals. Typically, the region is rigid, i.e. not pliable, which rigidity is due, at least in part, to the presence of non-intimal mineral associated with the vascular tissue. The mineral present in the subject region is generally a calcium mineral, and usually a calcium phosphate mineral. Where the mineral is a calcium phosphate, the mineral component typically includes one or more of hydroxyapatite, carbonated hydroxyapatite (dahllite) and calcium deficient hydroxyapatite.

Preparation of Target Region

The first step of the subject invention is generally the preparation of the target region of non-intimal vascular tissue. The target region is prepared by rendering it capable of being placed in an isolated local environment for subsequent contact with an acidic dissolution fluid, as described infra. The manner in which the target region is prepared varies depending on: (a) the nature of the target region; (b) whether demineralization occurs ex vivo or in situ; (c) the nature of the demineralization device employed; (d) whether the procedure is performed in an open or minimally invasive environment, and the like. Generally, preparation involves at least exposing the target region of vascular tissue, e.g. by removing overlaying tissues or structures. Where demineralization occurs ex vivo, preparation further includes removal of the section of vascular tissue that includes the target region from the host. Where the demineralization is to occur in situ, preparation at least includes rendering the target region accessible to the demineralization device to be employed, e.g. by removing overlying tissue to expose the target region of vascular tissue.

Preparation of Isolated Local Environment

An isolated local environment that includes the target region of non-intimal vascular tissue is then prepared. By isolated is meant that the local environment is physically separated from the remainder of the host in which the target vascular tissue is present. The isolated local environment may be produced in any convenient manner. Where the non-intimal vascular tissue is to be demineralized while separated from the host in which it is originally found, i.e. ex vivo, the isolated local environment may be produced in any container or well into which the target vascular tissue is placed.

In many preferred embodiments, however, the region of non-intimal vascular tissue is demineralized while still present in the host, i.e. the region of non-intimal vascular tissue is demineralized in situ. In such embodiments of the subject methods, the isolated local environment is generally produced with the assistance of a device that is capable of: (a) substantially isolating the region of non-intimal vascular tissue from the remainder of the host and (b) providing a local environment adjacent to the target region in which the pH can be reduced to the desired level, as described infra. Representative means for producing an isolated local environment comprising the region of vascular tissue to be demineralized are shown in FIGS. 2 to 5. For example, in FIGS. 2 to 3 is shown a device comprising a cup feature which is placed on top of the region to be demineralized, thereby producing a substantially isolated local environment that includes the target region. The cup may be secured to the vascular tissue as desired, e.g. by application of force or by the use of suction, as depicted in FIG. 2C. In another embodiment, the substantially isolated local environment that includes the region of non-intimal vascular tissue is produced by a device capable of enclosing a select portion or region of a vessel, e.g. an artery, such as the clam-shell device depicted in FIGS. 4 to 5. The devices depicted in FIGS. 2 to 5 are described in greater detail infra.

Maintaining pH at Subphysiologic Level

As mentioned above, the pH in the isolated local environment is maintained at a subphysiological level for a sufficient period of time for the desired amount of demineralization of the target region to occur. Typically, the pH is maintained at a value that does not exceed about 5, usually does not exceed about 4, and more usually does not exceed about 3. In many embodiments, the pH of the local environment ranges from between 0 and 1. Within the above range, the pH may be constant or variable over the course of the demineralization procedure, i.e. over the period of time during which the pH of the local environment is maintained at a subphysiological value.

The time period during which the local pH is maintained at a subphysiological level in the local environment that includes the target region is sufficient for the desired amount of demineralization to occur. As such, the pH of the local environment is maintained at a subphysiological value in the local environment for a period of time ranging from about 5 to 200 minutes, usually from about 10 to 100 minutes and more usually from about 10 to 30 minutes.

The pH of the local environment comprising the target region may be maintained at the requisite subphysiological level using any convenient protocol. Of particular interest in many embodiments is the use of a dissolution solution that is introduced into the local environment of the region and is capable of locally increasing the proton concentration in the local environment of the region. By capable of locally increasing the proton concentration is meant that the dissolution solution, upon introduction into the local environment of the region, as described in greater detail below, is capable of increasing the hydrogen ion concentration or $[H^+]$ in the local environment of the target region. In other words, the solution is capable of reducing the pH in the local environment of the target region to the requisite subphysiologic level for the required demineralization to occur.

Dissolution Solutions

A variety of different types of dissolution solutions may be employed in the subject methods, as long as the solutions are capable of increasing the proton concentration in the local environment of the target region to achieve the desired pH of subphysiologic level. In other words, any solution that is capable of providing the requisite subphysiologic pH in the local environment of the target region is suitable for use in the subject methods. Instead of using a single dissolution solution, a plurality of different dissolution solutions which vary by one or more parameters (e.g. type, pH, concentration etc.) may be sequentially introduced into the local environment of the target region. In such embodiments, the number of different dissolution solutions employed is at least 2, but generally does not exceed about 4 and usually does not exceed about 3.

One type of solution that finds use is an acidic dissolution or treatment solution. The acidic treatment solution will generally have a pH of less than about 6.5, where the pH is usually less than about 4.0 and more usually less than about 3.0. In many preferred embodiments, the pH ranges from 0 to 2, and usually 0 to 1. The acidic treatment solution can be composed of either a monobasic or a polybasic acid. Acids are "monobasic" when they have only one replaceable hydrogen atom and yield only one series of salts (e.g., HCl). Acids are "polybasic" when they contain two or more hydrogen atoms which may be neutralized by alkalies and replaced by organic radicals.

The acidic treatment solution can include a number of different types of acids, where the acids may or may not include a hydrocarbon moiety, i.e. a hydrogen bonded directly to a carbon atom. Suitable acids that lack a hydrocarbon moiety include halogen acids, oxy acids and mixtures thereof, where specific acids of interest of this type include, but are not limited to, hydrochloric, nitric, sulfuric, phosphoric, hydroboric, hydrobromic, carbonic and hydroiodic acids. In many embodiments, strong inorganic acids are preferred, e.g. hydrochloric, hydrobromic, hydroiodic, sulfuric, nitric, etc. The acid can be a concentrated acid, or can be diluted. Upon dilution, the concentration of an inorganic acid will generally be from about 10 N to about 0.01 N, preferably between 5.0 N to 0.1 N.

Also of interest are acids that include a hydrocarbon moiety, where such acids include, but are not limited to, any organic acid of one to six ($C_1$ to $C_6$) carbons in length. Organic acids of this type include, but are not limited to, formic, acetic, propionic, maleic, butanoic, valeric, hexanoic, phenolic, cyclopentanecarboxylic, benzoic, and the like. For an organic acid, the acid can be in concentrated form or can be diluted.

In many embodiments of the subject invention, the acid solution is hypertonic, by which is meant that the osmolarity of the solution is greater than that of a red blood cell, i.e. the osmolarity is greater than 300 mosmol. The solution may be rendered hypertonic by including any convenient component or components in the solution which provide for the desired elevated osmolarity.

Any convenient agent that is capable of increasing the osmolarity of the solution may be employed, where suitable agents include salts, sugars, and the like. In many embodiments, the agent that is employed to render the solution hypertonic is one or more, usually no more than three, and more usually no more than two, different salts. Generally, the salt concentration in these embodiments of the solution is at least about 100 mosmol, usually at least about 200 mosmol and more usually at least about 300 mosmol, where the concentration may be as high as 3000 mosmol or higher, depending on the particular salt being employed to render the solution hypertonic, where the solution may be saturated with respect to the salt in certain embodiments. Salts that may be present in the subject solutions include: NaCl, $MgCl_2$, Ringers, etc. where NaCl is preferred in many embodiments.

Of particular interest in many embodiments is the use of hydrogen chloride solutions. Hydrogen chloride solutions finding use in the subject methods have an HCl concentration that is sufficient to provide for the requisite pH in the local environment of the target region. Generally, the concentration of HCl in the solution ranges from about 0.001 to 1.0 N, usually from about 0.01 to 1.0 N and more usually from about 0.1 to 1.0 N. In many embodiments, the hydrogen chloride solution will further include one or more salts which make the solution hypertonic, as described above. In certain preferred embodiments, the salt is NaCl, where the concentration of NaCl in the solution is at least 0.05 M, usually at least 0.10 M, and more usually at least 0.15 M, where the concentration may be as high as 0.25 M or higher. In certain embodiments, the solution will be saturated with NaCl.

Dissolution solutions of interest include those described in PCT/US99/15918, the disclosure of which is herein incorporated by reference.

Reducing the pH of the Local Environment

As mentioned above, in the subject methods the dissolution solution is introduced into the local environment in which the target region is present in a manner sufficient to maintain the pH of the local environment at the requisite subphysiological level for a sufficient period of time for the desired amount of demineralization to occur. As such, the subject methods generally involve contacting the target region with the dissolution solution. The manner in which contact is achieved may be static or dynamic. By static is meant that a predetermined amount of dissolution solution is introduced into the local environment of the region and maintained in the local environment of the region for the entire treatment period, without the addition of further quantities of dissolution solution. By dynamic is meant that the dissolution solution is introduced into the local environment of the region one or more times, including continuously, during the treatment period.

During the dissolution procedure, protons from the local environment are removed as a result of the demineralization process. As such, it is often desirable to introduce the dissolution solution into the local environment of the region in a dynamic manner. Dynamic introduction of the dissolution solution typically involves flushing the local environment with the dissolution solution, where flushing involves a continuous flow of the dissolution solution across at least the surface of the target region, where the flow may be under pressure (e.g. where the fluid is emitted from the delivery device under enhanced pressure, as described in greater detail infra). In other words, the dissolution fluid is continuously flowed through the local environment of the target region for the period of time required for the desired amount of demineralization to occur. Simultaneously, fluid is removed from the local environment of the region such that the overall volume of fluid in the local environment of the region remains substantially constant, where any difference in volume at any two given times during the treatment period does not exceed about 50%, and usually does not exceed about 10%. In this manner, the pressure of the localized environment of the region is maintained at a substantially constant value, thereby minimizing traumatic impact on the vessel walls at the site of the target region.

Where the target region is flushed with the dissolution solution, the flow rate of the dissolution solution through the local environment of the region is generally at least about 1 volume/minute, usually at least about 2 volumes/minute and more usually at least about 10 volumes/minute, where the flow rate may be as great as 100 volumes/minute or greater, but usually does not exceed about 1000 volumes/minute and more usually does not exceed about 500 volumes/minute, where by "volume" is meant the volume of the local environment of the region.

When treatment involves dynamic flushing of the local environment of the target region, the total amount of dissolution fluid that is passed through the local environment that includes the target region during the treatment period typically ranges from about 0.5 to 50 liters, usually from about 0.5 to 5.0 liters and more usually from about 0.5 to 2.0 liters. In contrast, where a static methodology is employed, the total amount of dissolution fluid that is introduced into the local environment of the region ranges from about 100 ml to 1 liter, and usually from about 100 to 500 ml.

Additional Method Steps

In a number of embodiments of the subject methods, the above step of maintaining the local environment of the region at a subphysiological pH for a sufficient period of time for demineralization of the target region to occur is used in conjunction with one or more additional method steps in order to achieve the overall mineral reduction in the target region of non-intimal vascular tissue. Additional methods steps that may be present in the overall process include: contacting the target region with a solution designed to remove organic components, washing or rinsing the local environment of the target region, contacting the treated vascular site with one or more active agents, and the like.

Where one or more additional distinct solutions, such as priming solutions, washing solutions, organic phase dissolution solutions and the like are employed, as described below, such disparate solutions are generally introduced sequentially to the site of the target region. For example, the target region may be contacted with the following order of solutions: (1) washing solution to remove loose tissue from the target region; (2) organic phase dissolution solution, e.g. detergent solution such as cholic acid solution, to remove organic phases from the target region; (3) acidic dissolution solution to demineralize the target region; and (4) washing solution. Other sequences of solution application can also be employed.

Use of Organic Structure Dissolution Solutions

As mentioned above, in addition to the acidic dissolution solution, certain embodiments of the subject invention include a step of contacting the target region with a dissolution solution which serves to remove at least a portion of the non-mineral, typically organic, phase of the target region. The nature of this "organic phase dissolution solution" varies depending on the nature of the target region. Representative active agents that may be present in this organic phase dissolution solution include: oxidizing agents; organic solvents; lipid dissolving agents such as surfactants, e.g. TWEEN™, and detergents, where ionic detergents are of particular interest, e.g. cholic acid, glycocholic acid, benzylkonium chloride; enzymes, and the like.

Washing

In most embodiments, it is desirable to rinse or wash the local environment of the target region at least once of prior to or following treatment with the dissolution solution. The rinsing or washing solution can be any physiologically acceptable solution, such as a buffered solution of physiological pH, e.g. phosphate buffered saline.

Additional Agents

In certain embodiments, the local environment of the region is contacted with a wound healing or growth promoting solution that provides various growth factors to the target region to promote healing of the site. Growth factors of interest include: platelet derived growth factor, keratinocyte growth factor, basic fibroblast growth factor, leukocyte derived growth factor-2 (LDGF-2), transforming growth factor, epidermal growth factor (EGF), connective tissue growth factor, fibroblast growth factor 11, vascular IBP-like growth factor, epithelial cells growth factor, fibroblast growth factor 13, insulin-like growth factor-1, vascular endothelial growth factor (VEG-F), and the like.

Application of External Energy

In certain embodiments, external energy is applied to the target region to promote dissolution of the mineral component of the target region. Any means of applying external energy to the region may be employed. As such, jets or other such means which are capable of providing varying external forces to the target region sufficient to cause the mineral structures associated with, e.g. present on or in, the target region to break up or disrupt may be employed. Of particular interest in many embodiments is the use of ultrasound. The ultrasound can be applied during the entire time of contact of the target region vascular tissue with the acidic treatment solution, or the ultrasound can be applied for only part of the treatment period. In one embodiment, ultrasound is applied for several short periods of time while the dissolution treatment solution is contacted with the target region. There are several devices for the application of ultrasound to vascular tissue known to those of skill in the art. See e.g. U.S. Pat. Nos. 4,808,153 and 5,432,663, the disclosures of which are herein incorporated by reference. The ultrasound can be low frequency ultrasound.

Another means that may be employed to apply external energy to the target region during the dissolution process is to use a mechanical means of applying external energy. Mechanical means of interest include moving structures, e.g. rotating wires, which physically contact the target region and thereby apply physical external energy to the target region.

Demineralization of the Target Region

Maintenance of the local environment of the target region at a subphysiologic pH, as described above, results in at least partial demineralization of the region, i.e. at least a reduction of the calcium phosphate content of the target region. By reduction is meant that the total overall dry weight of calcium phosphate mineral associated with the target region is reduced or decreased, generally by at least about 50%, usually by at least about 75% and more usually by at least about 90%. In certain embodiments, substantially all of the calcium phosphate content of the target region may be removed, where by substantially all is meant at least about 90%, usually at least about 95% and preferably at least about 99% dry weight of the original calcium phosphate mineral associated with the region is removed.

DEMINERALIZATION DEVICES

Also provided by the subject invention are demineralization devices for use in demineralizing a target region of non-intimal vascular tissue, as described above. Demineralization devices of the subject invention at least include a means for substantially isolating the target region in a local environment in situ. As such, the subject devices at least include a means for producing an isolated local environment that contains the target region of non-intimal vascular tissue while the tissue is still attached to the host. The isolated local environment produced by the subject means should have a volume sufficient for fluid to be flushed through the local environment. As such, the volume of the isolated local environment produced by many embodiments of the subject devices typically ranges from about 1 to 100 ml, usually from about 1 to 15 ml and more usually from about 1 to 10 ml. In certain embodiments, the volume ranges from 10 to 100 ml or 5 to 15 ml or 1 to 10 ml. The above described means may take on a variety of configurations, including the cup configuration of the device depicted in FIGS. 2 to 3 and the "clam-shell" configuration of the devices depicted in FIGS. 4 to 5.

Figure 3A:
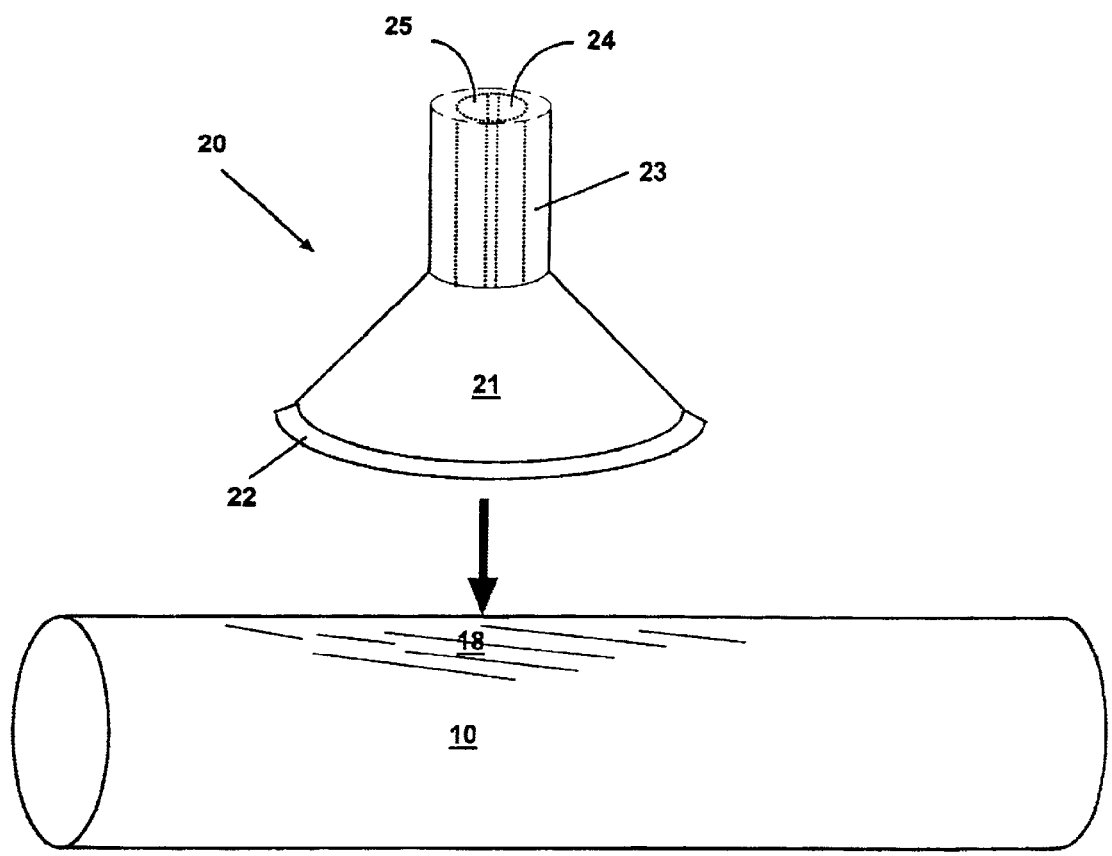
FIGS. 3A to 3C provide a depiction of the use of the device shown in FIGS. 2A to 2C in the demineralization of a region of non-intimal vascular tissue.
Figure 3B:
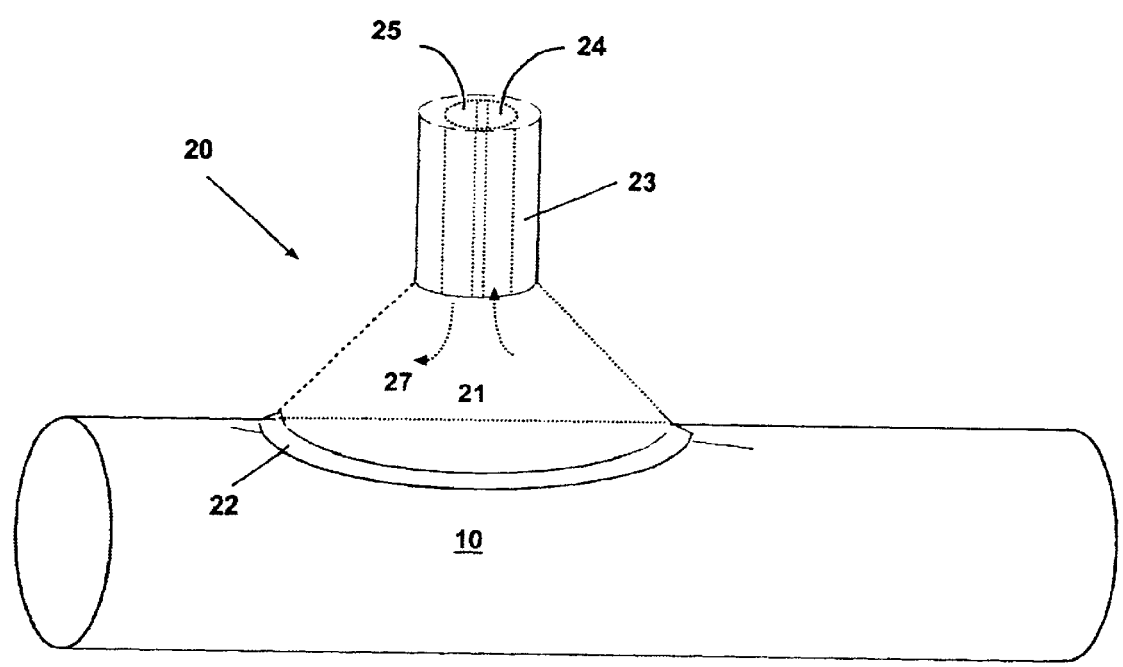
Figure 3C:
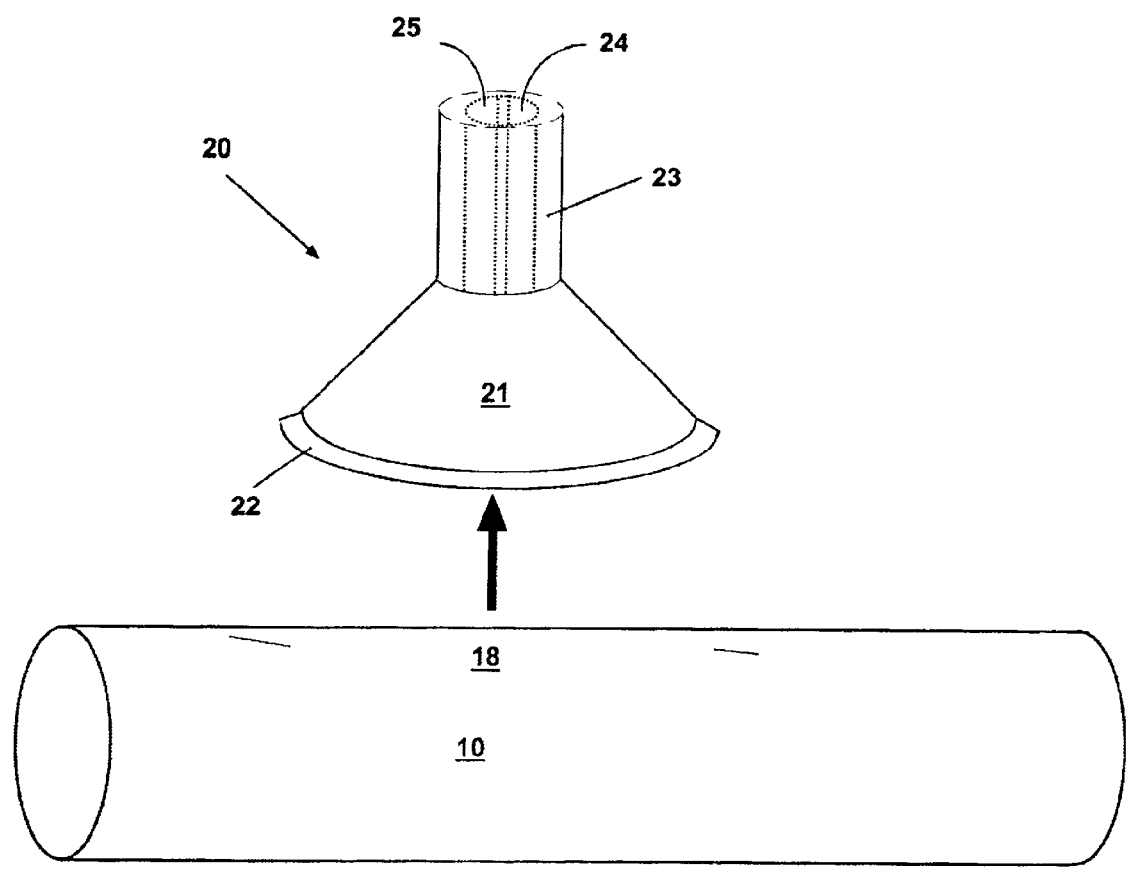

Turning to FIG. 2, FIG. 2 provides a view of a demineralization device according to the subject invention. Demineralization device 20 includes flared end 21 ending in circumferential edge 22, where the flared end defines a cup shape structure. At the end of 21 which has the smallest circumference is tubular structure 23 which houses the conduits 24 and 25 through which fluid is introduced into and extracted from the local environment produced upon contact of device 20 with a target region of vascular tissue, as depicted in FIGS. 3A to 3C. FIG. 2B provides an end on perspective of a first embodiment of the device shown generally in FIG. 2A. In FIG. 2B, the bottom side of flared end 21 is depicted. At the narrowest portion of flared end 21 are two openings, 24 and 25, through which fluid is introduced into and removed from a local environment produced by placement of the flared end of the device on a region of non-intimal vascular tissue. FIG. 2C provides a bottom view of another embodiment of the device shown in FIG. 2A, wherein the device further includes ports 26 along the periphery 22 of the flared end 21, which ports are operationally connected to a source of low pressure such that a suction force can be produced when the device is placed over the target region. In each of the depictions shown in FIGS. 2A to 2C, conduits 24 and/or 25 can be attached to a source of fluid, e.g. dissolution fluid, wash fluid, etc., during operation.

FIGS. 3A to 3C provide a representation of the use of a demineralization device as shown in FIG. 2. In FIG. 3A, vessel 10 is shown having a mineralized adventitia region 18. Demineralization device 20 is lowered onto the surface of vessel 10 covering target region 18, as shown in FIG. 3B, thereby producing an enclosed local environment bounded by flared end 21 and region 18 of vessel 10, where the enclosed local environment is shown in a cutaway view. Acidic dissolution fluid is then introduced through conduit 25 into the local environment in the direction of arrow 27. Fluid is also removed from the local environment via conduit 24 in the direction of the dashed arrow. In this manner, the local environment is flushed with the acidic dissolution solution, which maintains the enclosed local environment, as well as the target region 18, at a subphysiologic pH. The demineralization device may be secured to the surface of vessel 10 through the application of external downward pressure on the device, through the use of suction in embodiments such those depicted in FIG. 2C, or by any other convenient means.

Following a sufficient period of time for the desired amount of demineralization to occur, device 20 is then removed from the surface of vessel 10, exposing region 18 which is not demineralized. See FIG. 3C.

Figure 4A:
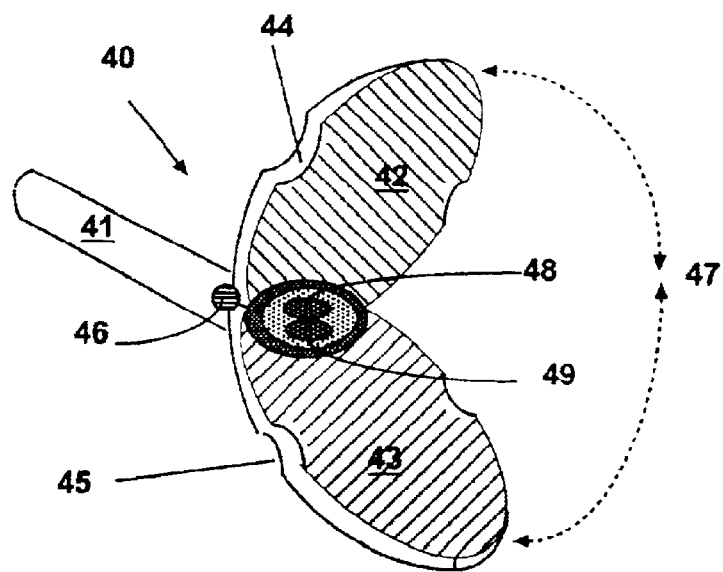
FIGS. 4A to 4B provide a depiction of a second embodiment of a 'clam-shell' device for practicing the subject methods.
Figure 4B:
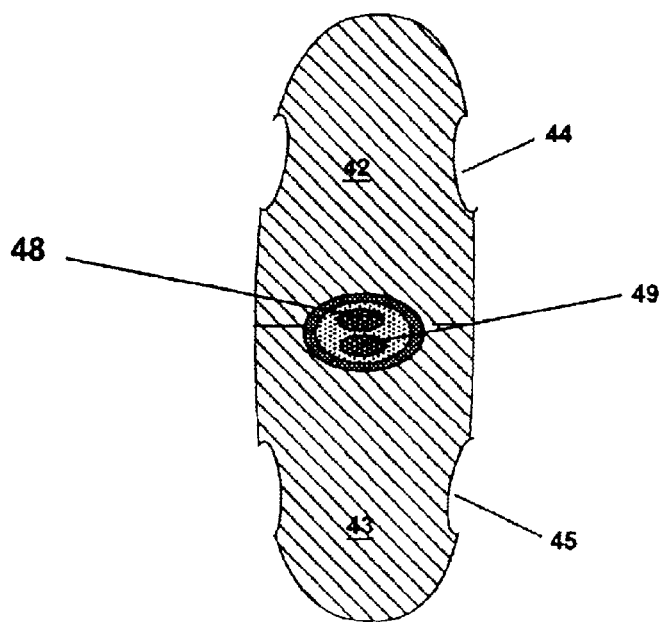

FIG. 4A provides a depiction of another embodiment of a demineralization device according to the subject invention identified as the "clam-shell" device. The device depicted in FIG. 4A is distinguishable from the device shown in FIGS. 2 to 3 in that it is capable of completely enclosing a region or domain of a vessel in situ, as opposed to just isolating a surface region of the vessel. In FIG. 4A, demineralization device 40 includes top portion 42 and bottom portion 43 which joined by a hinge region and are capable of being opened and closed in the direction indicated by the arrows 47. In both the top and bottom portions are cutouts or spaces for a vessel, e.g. an artery, to rest. At the juncture of the top and bottom portions is tube structure 41 which encloses fluid conduits which conduct fluid to and from the space defined upon closure of the top and bottom portions around a vessel, i.e. upon formation of an isolated local environment around a domain of the target vessel. FIG. 4B shows an end-on view of the device shown in FIG. 4A. In FIG. 4B, the underside of both bottom portion 43 and top portion 42 are shown, as well as cutouts 44 and 45. At the junction of the top and bottom portions, i.e. at the hinge region 46, are the openings of fluid conduits 48 and 49.

Figure 5:
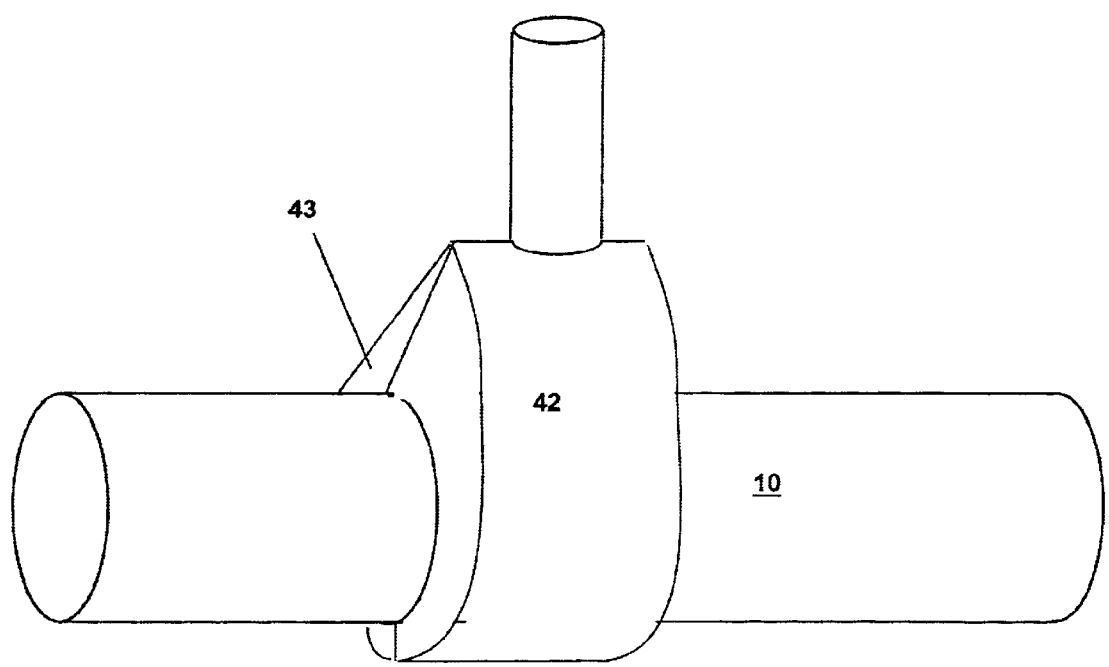
FIG. 5 provides a depiction of the use of the device shown in FIGS. 4A to 4B in the demineralization of a region of non-intimal vascular tissue.

FIG. 5 provides a representation of the device shown in FIGS. 4A and 4B enclosing a region of vessel 10 to thereby produce an isolated local environment that includes a region 18 (not shown) of vessel 10. In using the device as shown in FIGS. 4 to 5 to demineralize a region of vessel 10, the same process as described in connection with FIG. 3 is employed once the isolated local environment is produced by closing top and bottom portions 42 and 43 about vessel 10.

The devices may be fabricated from any convenient material which is capable of producing a device which meets the above parameters, e.g. allows for introducing of the device to the site of the target region; is physiologically compatible, at least during the treatment period; is capable of withstanding the solutions delivered by the device; etc. Fabricating a device according to the subject invention is well within the ability of those skilled in the art in view of the disclosure provided herein.

UTILITY

The subject methods find use in a variety of different applications in which it is desired to demineralize a region of non-intimal vascular tissue, e.g. where a mineral structure (s) is associated with a portion of non-intimal vascular tissue, such as media or adventitia.

One application in which the subject methods and devices find particular use in the demineralization of non-intimal vascular tissue in preparation for anastomosis, i.e. in the preparation of anastomosis sites, particularly for the preparation of end to side anastomosis sites, and more particularly in the preparation of the site of attachment of the graft vessel to the host vessel. Thus, where an anastomosis is to be performed, e.g. in a coronary artery bypass graft (CABG) procedure or in the bypass of a peripheral arterial occlusion, the subject methods and devices may be employed to demineralize the outer surface of the vessel at the anastomotic site, e.g. to make it more pliable and easier to work with during the anastomotic procedure, where the treated vessel is typically the host vessel.

The subject methods and devices may be employed on a variety of hosts. Generally such hosts are "mammals" or "mammalian," where these terms are used broadly to describe organisms which are within the class Mammalia, including the orders carnivore (e.g., dogs and cats), Rodentia (e.g., mice, guinea pigs, and rats), Lagomorpha (e.g. rabbits) and primates (e.g., humans, chimpanzees, and monkeys). In many embodiments, the hosts will be humans.

SYSTEMS

Also provided by the subject invention are systems for use in performing the subject methods. The systems of the subject invention include at least a demineralization device, such as the subject devices described above, and a dissolution fluid reservoir capable of holding or storing the dissolution fluid just prior to administration to the local environment of the target region. In addition, the subject systems will typically include a means for moving the dissolution fluid through the fluid introduction means to the local environment of the region, where such means is typically a pump, large syringe, and the like. The system may also conveniently include a means for maintaining the pressure and/or temperature of the dissolution fluid at a desired value. In addition, the subject systems typically include a means for removing fluid from the local environment of the target region, e.g. a second pumping means or suction means. The above elements of the subject system may conveniently be present in a housing fabricated of a suitable material.

KITS

Also provided are kits for use in performing the subject methods. The kits typically comprise at least the dissolution fluid to be used in the subject methods, such as a hydrochloric acid solution as described above, where the solution may be present in a storage means, such as a flexible bag or a rigid container. For kits that are to be used in methodologies in which the fluid is flushed through the local environment of the target region, the amount of dissolution fluid present in the kit ranges from about 1 to 500 liters, usually from about 10 to 200 liters and more usually from about 50 to 100 liters. For kits that are to be used in static methodologies, the amount of dissolution fluid present in the kit generally ranges from about 100 ml to 1 liter and usually from about 100 ml to 500 ml. Alternatively, the kit may comprise precursors of the dissolution solution for use in preparing the solution at the time of use. For example, the precursors may be provided in dry form for mixing with a fluid, e.g. water, at the time of use. Also present in the kit may be a demineralization device, as described supra. In addition to the dissolution fluid or precursors thereof, the kit may further comprise one or more additional fluids (or dry precursors thereof), such as an organic phase dissolution solution, a washing solution, and the like. Finally, the kits will include instructions for practicing the subject methods, where such instructions may be present on one or more of the kit components, the kit packaging and/or a kit package insert.

The following examples are offered by way of illustration and not by way of limitation.

EXPERIMENTAL

I. Mineral Dissolution Assays

A. Norian SRS® cement (obtained from Norian Corporation, Cupertino, Calif.) is prepared according to the manufacturer's instructions. The resultant paste is placed into Teflon mold rings and allowed to set to produce dahllite disks. The disks are then contacted with the following solutions: 0.1 M HCl, 1.0 M HCl, concentrated HCl, 0.1 M HCl+0.01 M EDTA, 1.0 M HCl+0.01 M EDTA, concentrated HCl+0.1 M EDTA, 0.1 M $H_2SO_4$, 1.0 M $H_2SO_4$, 0.1 M $H_2SO_4$+0.01 M EDTA, 1.0 M $H_2SO_4$+0.1 M EDTA, 1.0 M formic acid, concentrated formic acid, 1.0 M formic acid+0.1 M EDTA, 1.0 M acetic acid, concentrated acetic acid, 1.0 M acetic acid and 0.1 M EDTA, 1.0 M succinic acid, 1.0 M succinic acid+0.1 M EDTA; 0.1 M carbonic acid; and 1.0 M carbonic acid. A dissolution graph is then prepared for each solution which plots $Ca^{2+}$ concentration over time. By comparing the different dissolution graphs, the solubility of dahllite in different dissolution solutions is compared.

B. Dissolution of Bolus of Dahllite in 0.05N HCl with Various Ionic Strengths Using Pump at 69 ml/min 1. Introduction Six dissolution experiments were conducted to determine the affect of ionic strength on the dissolution rate of carbonated hydroxyapatite in HCl. According to the Kinetic Salt Effect theory, oppositely charged ions react more slowly as the ionic strength of the solution is increased because the electrostatic attraction between the reacting ions is decreased. The object of this experiment was to determine if the theory holds for the dissolution reaction of carbonated hydroxyapatite with HCl.

2. Experimental

A Cole-Parmer peristaltic pump (model #7520-35) was used to deliver the demineralizing 0.05N HCl solution with varying NaCl concentrations to the sample of carbonated hydroxyapatite (i.e. dahllite), $Ca_{8.8}(HPO_4)_{0.7}(PO_4)_{4.5}(CO_3)_{0.7}(OH)_{1.3}$, in the form of a spherical bolus. In each case, a 100±3 mg bolus (dry weight) of carbonated hydroxyapatite was soaked in deionized water until there was no further weight gain. This weight was taken to be the initial weight of the bolus. The bolus was then transferred to a 12 ml disposable liquid transfer pipette and a peristaltic pump with a rubber stopper on one end of the tubing was attached. Solutions were pumped through the pipette past the bolus at a rate of approximately 69 ml/min in 5 minute time intervals and the weight of the bolus was measured at the end of each interval. The dissolution process was continued until the weight of the bolus was less than 5 mg. The NaCl concentrations used were: 0, 5.8 (isotonic), 11.6, and 25 g/L.

3. Results

The results of the six dissolution experiments are tabulated below. A table of the respective half-lives follows. The wet weight of the bolus at t=0 is represented by m(o), and m(t) is the weight at a given time interval (m=mass).

TABLE 1

Dissolution of Bolus of 0.05 N HCl with Various Ionic Strengths

| | log[m(t)/m(0)] | | | | | |
|---|---|---|---|---|---|---|
| Time (min) | No salt | No salt (2) | 5.8 g NaCl | 5.8 g NaCl(2) | 11.6 g NaCl | 25 g NaCl |
| 0.0 | 0.0000 | 0.0000 | 0.0000 | 0.0000 | 0.0000 | 0.0000 |
| 5.0 | −0.0569 | −0.0982 | −0.0789 | −0.0822 | −0.1209 | −0.1300 |
| 10.0 | −0.1374 | −0.2121 | −0.1926 | −0.1803 | −0.2287 | −0.3014 |
| 15.0 | −0.2403 | −0.3212 | −0.3322 | −0.2906 | −0.3973 | −0.5792 |
| 20.0 | −0.3594 | −0.4491 | −0.5195 | −0.4514 | −0.6717 | |
| 25.0 | −0.4765 | −0.5907 | −0.8683 | −0.6736 | | |
| 30.0 | −0.6273 | −0.7788 | | −1.2653 | | |
| 35.0 | −0.8154 | −1.0740 | | | | |

Half-lives for the Dissolution of Bolus in 0.05 N HCl

| Half-life (min) | No salt | No salt (2) | 5.8 g NaCl | 5.8 g NaCl(2) | 11.6 g NaCl | 25 g NaCl |
|---|---|---|---|---|---|---|
| | 15.8 | 12.7 | 11.6 | 11.8 | 10.5 | 8.8 |

4. Discussion and Conclusion

The half-life data and log[m(t)/m(0)] vs. time show that increasing the ionic strength of the solution increases the dissolution rate. This contradicts the Kinetic Salt Effect theory which says that increasing the ionic strength of a solution decreases the reaction rate between oppositely charged ions due to a decrease in electrostatic attraction between the ions. In this case, $Na^+$ and $Cl^-$ ions should theoretically decrease the electrostatic attraction between $H^+$ and both $HPO4^{2+}$ and $PO4^{3+}$ and slow the rate of dissolution.

C. Dissolution of Bolus in HCl Solutions of Various pH

1. Introduction

Eight sets of dissolution experiments were conducted to determine the affect of pH on the dissolution rate of carbonated hydroxyapatite in HCl. It was predicted that a decrease in pH (increase in $H^+$) should increase the rate of dissolution. In addition, three different methods of dissolution were used to see how altering the method would affect the dissolution rate.

2. Experimental

For each experiment, a 100±3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further weight gain and this weight was taken to be the initial weight of the bolus. Descriptions of the three dissolution methods are below. For each set of experiments, nine pH levels were studied.

i. Stirring

For the stirring experiments, the bolus was placed in a beaker with a volume of HCl solution that provided twice the stoichiometric number of protons necessary to dissolve the carbonated hydroxyapatite. A stir bar of appropriate size was added to the beaker and the solution was stirred on an IKA Labortechnik stir plate on a setting of 6. For each experiment, the weight of the bolus was measured at time intervals appropriate for the pH of the solution used until the weight of the bolus was less than 5 mg. pK was calculated from the slope of the linear regression line for each set of data points using the following formula:

$$pK = -\log[1.533 * \text{slope}]$$

ii. Sonication

Sonication experiments employed a Branson Sonifier 450 to deliver ultrasound to the HCl solution. Power outputs of 9 Watts, 35 Watts, and 53 Watts were used. The solutions were also stirred on an IKA Colorsquid stir plate on a setting of 2 to ensure complete mixing. The bolus was placed in a beaker with a volume of HCl solution that provided twice the stoichiometric number of protons necessary to dissolve the it, and weight measurements were made at time intervals appropriate for the pH of the solution until the weight was less than 5 mg. pK was calculated as it was for the stirring experiments.

iii. Pump

A Cole-Parmer peristaltic pump (model #7520-35) was used to deliver the HCl solution to bolus. The bolus was placed in a 12 ml disposable liquid transfer pipette and the peristaltic pump with a rubber stopper on one end of the tubing was attached. Solutions were pumped through the pipette past the bolus at rates of approximately 16 ml/min, 33 ml/min, 69 ml/min, and 110 ml/min. Weight measurements were made at appropriate time intervals until the weight was less than 5 mg, and pK was calculated as before.

3. Results

The results of the eight sets of dissolution experiments are included in Table 2 below. Graphs were also generated from the observed data. Rate measurements for 0.8N, 0.6N and 0.075N were not taken for the sonication and pump experiments because the slope of the pK vs. pH linear regression line for the stirring experiment was relatively unchanged by including these points. Note that a lower pK indicates a faster dissolution rate.

the pump flow rate was increased. The maximum flow rate for the peristaltic pump that was used was 110 ml/min, but it is anticipated that a faster dissolution rate may be achieved by using a faster pump. The faster rate may be attributed to the fact that a larger volume of solution (more than double the stoichiometric number of protons) must be used with the pump, and that the bolus is always exposed to fresh solution which is equivalent to ultimate mixing. The stream of solution may also mechanically remove particles from the bolus.

One final observation from the pK vs. pH graph is that differences in rate for the different methods decrease as pH decreases. In other words, rates vary less at pH 0 and vary more at pH 2. Therefore, for solutions of higher proton concentration, the rate of dissolution is less dependent on the method employed.

D. Dissolution of Bolus in HCl Solutions using Ultrasound

1. Introduction

Six sets of dissolution experiments were conducted to determine the effect of Ultrasound on the dissolution rate of carbonated hydroxyapatite in HCl. It was predicted that an increase in ultrasonic power should increase the rate of dissolution due to an increase in mixing of the solution.

2. Experimental

For each experiment, a 100±3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further

TABLE 2 pKs Resulting from Dissolution of Bolus with Various HCl Solutions and Various Dissolution Methods

| HCl concentration (N) | pH | Stirring | Sonication 9W | Sonication 35W | Sonication 53W | Pump 16 ml/min | Pump 33 ml/min | Pump 69 ml/min | Pump 110 ml/min |
|---|---|---|---|---|---|---|---|---|---|
| 1.000 | 0.000 | 0.7189 | 0.1997 | 0.2634 | 0.3557 | 0.4190 | 0.2710 | 0.2392 | 0.2069 |
| 0.800 | 0.097 | 0.8204 | | | | | | | |
| 0.600 | 0.222 | 1.1122 | | | | | | | |
| 0.400 | 0.398 | 1.2840 | 0.7086 | 0.5689 | 0.6252 | 0.8400 | 0.5717 | 0.4875 | 0.4195 |
| 0.200 | 0.699 | 1.6950 | 0.9987 | 0.8799 | 0.6922 | 1.1140 | 0.9887 | 0.7103 | 0.7015 |
| 0.100 | 1.000 | 1.8600 | 1.4970 | 1.1693 | 1.1146 | 1.2390 | 1.1524 | 1.0674 | 0.8288 |
| 0.075 | 1.125 | 2.0310 | | | | | | | |
| 0.050 | 1.301 | 1.9440 | 1.9612 | 1.4658 | 1.5364 | 1.5020 | 1.4340 | 1.2938 | 0.9704 |
| 0.001 | 2.000 | 2.2440 | 2.3607 | 2.3773 | 2.0659 | 2.3240 | 1.9982 | 1.8080 | 1.6649 |

4. Discussion and Conclusion

Several conclusions may be drawn from the results of these experiments. First, the positive slopes of the lines on the pK vs. pH graph (not shown) show that a decrease in pH of the solution (increase in $H^+$) results in an increase in dissolution rate (decrease in pK) as expected. The dissolution involves $H^+$, $HPO_4^{2+}$ and $PO_4^{2+}$ ions, so it makes sense that increasing $H^+$ should increase the dissolution rate.

Both sonication and the pump gave faster dissolution rates than stirring alone. This is most likely due to the fact that sonication and pumping provide better mixing of the solution, effectively removing any layer of dissolved or reprecipitated material from the immediate area surrounding the bolus.

For the sonication experiments, increasing the ultrasonic power increased the rate of dissolution. When ultrasound was used, tiny craters in the surface of the bolus were observed. Increasing the ultrasonic power may help dissolution by either increasing the surface area due to these craters, increasing the mixing of the solution, or both. It may also dislodge particles from the surface of the bolus that are not yet dissolved.

Of the three dissolution methods studied, the pump gave the fastest dissolution rate. The rate consistently increased as weight gain and this weight was taken to be the initial weight of the bolus. The bolus was placed in a beaker with a volume of HCl solution that provided twice the stoichiometric number of protons necessary to dissolve it, and a Branson Sonifier 450 was employed to deliver ultrasound to the solution. Various HCl solutions were employed. The 0.1N, 0.05N, and 0.01N HCl solutions were made isotonic (300 mOsmol) with NaCl. Power outputs of 9 Watts, 35 Watts, and 53 Watts were used. The solutions were also stirred on an IKA Colorsquid stir plate on a setting of 2 to ensure complete mixing. Weight measurements were made at time intervals appropriate for the pH of the solution until the weight was less than 5 mg. pK was calculated from the slope of the linear regression line for each set of data points using the following formula:

$$pK = -\log[1.533 * slope]$$

3. Results

The results of the six sets of dissolution experiments are tabulated below in Table 3. Note that a lower pK indicates a faster dissolution rate.

TABLE 3

| Ultrasonic Power (Watts) | 1 N HCl | 0.4 N HCl | 0.2 N HCl | 0.1 N HCl | 0.05 N HCl | 0.01 N HCl |
|---|---|---|---|---|---|---|
| pKs Resulting from Dissolution of Bolus Using Ultrasound | | | | | | |
| 9 | 0.1997 | 0.7086 | 0.9987 | 1.497 | 1.9612 | 2.3607 |
| 35 | 0.2634 | 0.5689 | 0.8799 | 1.1693 | 1.4658 | 2.3773 |
| 53 | 0.3557 | 0.6252 | 0.6922 | 1.1146 | 1.5364 | 2.0659 |
| Half-lives (in min) Resulting from Dissolution of Bolus Using Ultrasound | | | | | | |
| 9 | 1.1 | 3.6 | 6.8 | 18.5 | 48.3 | 130.5 |
| 35 | 1.2 | 2.2 | 4.3 | 8.9 | 15.6 | 130.7 |
| 53 | 1.2 | 2.8 | 3 | 7.9 | 19.3 | 64.2 |

4. Discussion and Conclusion

The half-life data table shows that when the ultrasonic power was increased from 9 Watts to 35 Watts, the rate of dissolution increased for all solutions except 1N HCl and 0.01N HCl for which the rates remained relatively unchanged. The 1N HCl solution dissolves the bolus so quickly that any minor rate changes are difficult to observe. It is unclear why there was no observable increase in dissolution rate for the 0.01N solution. When the ultrasonic power was increased to 53 Watts, dissolution rates increased for all solutions except 1N and 0.4N, for which rates remained relatively unchanged, and 0.05N for which the rate decreased slightly. The results indicate that increasing the ultrasonic power increased the dissolution rate except when the rate is already so fast that minor changes are difficult to observe.

E. Dissolution of Bolus in HCl Solutions Using Pump

1. Introduction

Six sets of dissolution experiments were conducted to determine the effect of pump flow rate on the dissolution rate of carbonated hydroxyapatite in HCl. It was predicted that an increase in flow rate should increase the rate of dissolution due to an increase in exposure to protons.

2. Experimental

For each experiment, a 100±3 mg (dry weight) sample of carbonated hydroxyapatite, $Ca_{8.8}(HPO_4)_{0.7}(PO_4)_{4.5}(CO_3)_{0.7}(OH)_{1.3}$, in the form of a spherical bolus was used. The bolus was soaked in deionized water until there was no further weight gain and this weight was taken to be the initial weight of the bolus. The bolus was placed in a 12 ml disposable liquid transfer pipette and a Cole-Parmer peristaltic pump (model #7520-35) with a rubber stopper on one end of the tubing was attached. Various HCl solutions were pumped through the pipette past the bolus at rates of approximately 16 ml/min, 33 ml/min, 69 ml/min, and 110 ml/min. The 0.1N, 0.05N, and 0.01N HCl solutions were made isotonic (300 mOsmol) with NaCl. Weight measurements were made at time intervals appropriate for the pH of the solution until the weight was less than 5 mg. pK was calculated from the slope of the linear regression line for each set of data points using the following formula:

$$pK = -\log[1.533 * \text{slope}]$$

3. Results

The results of the six sets of dissolution experiments are tabulated below. Note that a lower pK indicates a faster dissolution rate.

TABLE 4

| Pump Flow Rate (ml/min) | 1 N HCl | 0.4 N HCl | 0.2 N HCl | 0.1 N HCl | 0.05 N HCl | 0.01 N HCl |
|---|---|---|---|---|---|---|
| pKs Resulting from Dissolution of Bolus Using Pump | | | | | | |
| 16 | 0.4190 | 0.8400 | 1.1140 | 1.2390 | 1.5020 | 2.3240 |
| 33 | 0.2710 | 0.5717 | 0.9887 | 1.1524 | 1.4340 | 1.9982 |
| 69 | 0.2392 | 0.4850 | 0.7103 | 1.0674 | 1.2938 | 1.8084 |
| 110 | 0.2069 | 0.4195 | 0.7015 | 0.8288 | 0.9704 | 1.6649 |
| Half-lives (in min) Resulting from Dissolution of Bolus Using Pump | | | | | | |
| 16 | 1.5 | 3.9 | 7.6 | 10.0 | 21.1 | 110.5 |
| 33 | 1.1 | 2.2 | 5.5 | 9.2 | 15.3 | 61.5 |
| 69 | 1.0 | 1.5 | 3.0 | 6.7 | 11.6 | 38.8 |
| 110 | 0.8 | 1.6 | 2.8 | 4.8 | 6.4 | 29.2 |

4. Discussion and Conclusion

The data show an obvious increase in dissolution rate as the pump speed is increased. 110 ml/min was the fastest flow rate that could be attained with this pump, however it is likely that the dissolution rate would continue to increase with a faster pump. The increase in rate may be attributed to the increase in exposure of the bolus to protons. Mechanical removal of surface particles may also play a role.

II. Formulations (A) Solution A=1.0 N HCl+0.25 M NaCl.
(B) Solution B=0.5 N HCl+0.25M NaCl.
(C) Solution C=0.1 N HCl+0.05 M NaCl.
(D) A suitable formulation for acidic treatment under a constant flow rate comprises:
  Formic acid (concentrated) . . . 10%
  Sodium dodecyl sulfate (SDS) . . . 0.1%
  $H_2O$ . . . qs . . . 100%
(E) An alternative formulation for acidic treatment under a constant flow rate comprises:
  HCl (concentrated) . . . 10%
  EDTA . . . 0.1%
  $H_2O$ . . . qs . . . 100%
(F) An alternative formulation for acidic treatment under a constant flow rate comprises:
  Phosphoric acid (concentrated) . . . 10%
  $H_2O$ . . . qs . . . 100%
(G) An alternative formulation for acidic treatment under a constant flow rate comprises:
  Sulfuric acid (concentrated) . . . 10%
  $H_2O$ . . . qs . . . 100%
(H) An alternative formulation for acidic treatment under a slower rate or under static conditions comprises:
  Tris HCl . . . 0.1 M
  pH adjusted to 4.2 with concentrated HCl.

It is evident from the above results and discussion that the above invention provides a simple and effective means for demineralizing non-intimal vascular tissue. As such, the subject invention finds use in a variety of different applications, such as the preparation of vascular anastomotic sites. Accordingly, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of reducing the mineral content of a region of non-intimal vascular tissue, said method comprising:
   (a) producing an isolated local environment that includes said region;
   (b) introducing an acidic dissolution fluid having a subphysiologic pH into said isolated local environment; and
   (c) maintaining the isolated local environment of said region at a subphysiologic pH for a period of time sufficient for the mineral content of said region to be reduced so that the mineral content of said region of non-intimal vascular tissue is reduced.

2. The method according to claim 1, wherein said introducing comprises flushing said local environment with said dissolution fluid.

3. The method according to claim 1, wherein said method further comprises applying energy to said region.

4. The method according to claim 1, wherein said mineral is a calcium mineral.

5. The method according to claim 4, wherein said calcium mineral is a calcium phosphate.

6. A method of reducing the calcium phosphate content of a region of non-intimal vascular tissue, said method comprising:
   (a) producing an isolated local environment that includes said region; and
   (b) flushing said region with an acidic dissolution fluid having a subphysiologic pH capable of increasing the proton concentration in the isolated local environment of said region so that the calcium phosphate content of said region is reduced.

7. The method according to claim 6, wherein said acidic dissolution fluid comprises and an inorganic acid.

8. The method according to claim 7, wherein said inorganic acid is a strong acid.

9. The method according to claim 8, wherein said strong acid is hydrochloric acid.

10. The method according to claim 6, wherein said acidic dissolution fluid is hypertonic.

11. A method for reducing the calcium phosphate content of a region of non-intimal vascular tissue, said method comprising:

producing an isolated local environment comprising said region;

flushing said local environment with an acidic dissolution fluid having a subphysiologic pH for a period of time sufficient to reduce the calcium phosphate content of said region, wherein said acidic dissolution fluid comprises a strong acid so that the calcium phosphate content of said region is reduced.

12. The method according to claim 11, wherein said strong acid is hydrochloric acid.

13. The method according to claim 11, wherein said acidic dissolution fluid is hypertonic.

14. The method according to claim 11, wherein the pH of said acidic dissolution fluid ranges from 0 to 2.

15. The method according to claim 11, wherein said method further comprises applying energy to said calcified region.

* * * * *